United States Patent [19]

Jarvis et al.

[11] Patent Number: 5,179,007
[45] Date of Patent: Jan. 12, 1993

[54] METHOD AND VECTOR FOR THE PURIFICATION OF FOREIGN PROTEINS

[75] Inventors: Donald L. Jarvis; James C. Carrington, both of Bryan, Tex.

[73] Assignee: The Texas A & M University System, College Station, Tex.

[21] Appl. No.: 377,438

[22] Filed: Jul. 7, 1989

[51] Int. Cl.⁵ .................. C12P 21/06; C12N 15/62; C12N 15/85; C12N 5/16

[52] U.S. Cl. .................. 435/68.1; 435/69.1; 435/69.8; 435/320.1; 435/240.2; 435/69.7; 530/413; 935/48; 935/51; 935/70

[58] Field of Search ............. 435/320.1, 235.1, 69.1, 435/240.2, 69.7, 68.1; 530/413; 935/48, 51, 70

[56] References Cited

U.S. PATENT DOCUMENTS

| | | | |
|---|---|---|---|
| 4,769,326 | 9/1988 | Rutter | 435/69.7 X |
| 4,851,341 | 7/1989 | Hopp et al. | 435/69.7 X |
| 4,870,023 | 9/1989 | Fraser et al. | 435/69.3 X |

OTHER PUBLICATIONS

Jarvis, D. L. et al. 1991, *Virology* vol. 185 pp. 795–810.
Mori, H. et al. 1989, *J. Gen. Virol.* vol. 70 pp. 1885–1888.
Akiyoshi, D. et al. 1985 *Virology* vol. 141 pp. 328–332.
Scopes, R. K. 1987 *Protein Purification: Principles and Practices* 2nd edition, Springer-Verlag, N.Y. pp. 26–28.
Smith, G. E. et al. 1983, *Molecular and Cellular Biology*, vol. 3 pp. 2156–2165.
Luckow, V. A. et al. 1988, *Virology*, vol. 167 pp. 56–71.
Marumoto, Y. et al. 1987, *Journal of General Virology*, vol. 68 pp. 2599–2606.
Waxman, L. et al. 1987, In: *Protein Purification: Micro to Macro*, ed. R. Burgess, Alan R. Liss Inc., pp. 459–473.
Wilson, G. L. et al. 1975, *Journal of Biological Chemistry*, vol. 250 pp. 8604–8613.
Dingwall et al., Ann. Rev. Cell Biol. 2:367–390 (1986).
Silver et al., R. C. Das and P. W. Robbins (eds.) 749–769 (1988).
Lanford et al., Cell 37:801–813 (1984).
Kalderon et al., Nature 311:33–38 (1984).
Richardson et al., Cell 44:77–85 (1986).
Wychowski et al., Gene 37:63–71 (1985).
Lyons et al., Mol. Cell Biol. 7:2541–2456 (1987).
Davey et al., Cell 40:667–675 (1985).
Jones et al., EMBO J. 5:2371–2376 (1986).
Greenspan et al., J. Virol. 62:3020–3026 (1988).
Burglin et al., EMBO J. 6:2617–2625 (1987).
Hall et al., Cell 36:1057–1065 (1984).
Silver et al., PNAS 82:5951–5955 (1984).
Goldfarb et al., Nature 322:641–644 (1986).
Lanford et al., Cell 46:575–582 (1986).
Newmeyer et al., Cell 52:641–653 (1988).
Richardson et al., Cell 52:655–664 (1988).
Adam et al., Nature 337:276–279 (1989).
Dingwall et al., Cell 30:449–458 (1982).
Zoller et al., Methods Enzymol. 100:468–500 (1983).
Krausslich et al., Ann. Rev. of Biochem. 57:701–754 (1988).
Carrington et al., Virology 160:355–362 (1987).
Carrington et al., J. of Virol. 61:2540–2548 (1987).
Carrington et al., PNAS 85:3391–3395 (1988).
Carrington et al., J. of Virol. 62(7):2313–2320 (1988).
Dougherty et al., EMBO J. 7:1281–1287 (1988).

*Primary Examiner*—Richard A. Schwartz
*Assistant Examiner*—Mary E. Mosher

[57] ABSTRACT

The present invention provides an method for isolating and purifying recombinantly produced proteins. This invention involves the use of an expression vector which includes a nuclear targeting signal sequence which effectively directs newly synthesized proteins to the nucleus; a cleavage recognition sequence which cleaves specifically at a pre-determined cleavage site after addition of a viral enzyme; and a cDNA sequence which codes for a desired protein. Specifically the production and isolation of a desired protein is accomplished through the use of lepidopteran cells transfected or infected with recombinant baculovirus expression vector comprising a polyhedrin gene derived nuclear targeting signal sequence and a cleavage recognition sequence derived from a potyvirus polyprotein. The newly synthesized proteins are directed into the nucleus whereupon nuclear protein is extracted from the nucleus. Thereafter the desired protein is bound to an affinity matrix embedded with antibodies directed against the nuclear targeting sequence. Afterwards the desired protein is cleaved from the affinity matrix with the addition of a viral enzyme.

11 Claims, 3 Drawing Sheets

+ + + + + +
lys tyr tyr lys asn leu gly ala val ile lys asn ala lys arg lys lys his
19  20  21  22  23  24  25  26  27  28  29  30  31  32  33  34  35  36

CYTOPLASMIC           NUCLEAR

→ REGENERATE COLUMN (EG. HIGH SALT WASH)

→ HARVEST PRODUCT, REGENERATE COLUMN

METHOD AND VECTOR FOR THE PURIFICATION OF FOREIGN PROTEINS

The government may own certain rights in the present invention pursuant to National Institutes of Health grant number AI27832(JCC).

BACKGROUND OF THE INVENTION

1. Field of Invention

The present invention relates to the production and purification of proteins, from eukaryotic cells, using a recombinant expression system. In particular aspects, for the production and purification of proteins, this invention relates to the use of a nuclear targeting recognition signal sequence, which specifically directs the newly synthesized proteins into the nucleus from the cytoplasm, in combination with a viral enzyme which allows cleavage of the synthesized protein at a specific cleavage recognition sequence, thus freeing a desired protein product.

2. Description of the Related Art

Through the use of recombinant DNA technologies, the capabilities of producing genetically engineered proteins have increased in the recent years. However, with these new capabilites, problems have arisen in the area of protein production and purification. One problem involves the purification of the protein while maintaining its functionality and preventing degradation. Producing large quantities of a specific protein is of little use if the protein degrades during the purification regimen or if the protein can not readily be purified in a manner in which the protein's functionality is maintained.

With these problems in mind, the inventors intended to establish a production protocol that could be used for a variety of proteins. The inventors also disclosed a generic purification schema that could be applied to these various proteins with little or no modifications required.

BACULOVIRUSES

Baculoviruses are double-stranded DNA-containing viruses that infect a variety of different insect species. The nuclear polyhedrosis viruses, which comprise subgroup A of the Family Baculoviridae, induce the formation of paracrystalline occulsion bodies in the nuclei of infected host cells. These occlusion bodies are composed primarily of a single viral protein which is expressed at very high levels (polyhedrin). In later stages of the infection cycle, polyhedrin may account for more than 50% of the total protein. The polyhedrin gene has been cloned and sequenced and its unique features have provided the basis for the development of a series of baculovirus expression vectors (BEVs: Summers, M. D. and Smith, G. E., TAES Bull. 1555 (1987); Luckow, V. A. and Summers, M. D., Biotechnology 6:47-55 (1988); Miller, L. K., Ann. Rev. Microbiol. 42:177-179 (1988); U.S. Pat. No. 4,745,051, G. E. Smith and M. D. Summers (Filed May 27, 1983; Issued May 17, 1988)).

BACULOVIRUS EXPRESSION VECTORS (BEVs)

BEVs are recombinant baculoviruses in which the coding sequence for polyhedrin has been replaced with the coding sequence for a desired protein. In general, this approach involves the construction and isolation of recombinant baculoviruses in which the coding sequence for the chosen gene has been inserted behind the promoter for the nonessential polyhedrin viral gene (Pennica, et al, Mol. Cell. Biol. 4:399-406 (1984); Smith, et al, L. Virol. 46:584-593 (1983); Smith, G. E. and M. D. Summers, Mol. Cell. Biol. 3:2156-2165 (1983); U.S. Pat. No. 4,745,051, G. E. Smith and M. D. Summers (Filed May 27, 1983; Issued May 17, 1988)).

Several advantages may be enjoyed when employing the baculovirus expression vector (BEV) system. One of these advantages is the strong polyhedrin promoter which directs a high level of expression of the insert (protein of choice). The newly expressed protein accumulates in large amounts within these infected insect cells. Thus, as a result of the relative strength of the polyhedrin promoter, many different gene inserts can be expressed at very high levels.

In addition to providing a high expression level, another advantage of the BEV system, is the ease with which these baculoviruses are produced and identified. This process begins by co-transfecting wild-type viral DNA and a "transfer vector" into susceptible host cells. A transfer vector is defined as a bacterial plasmid which contains a desired gene directly 3' to the polyhedrin promoter, as well as long viral sequences flanking the promoter on the 5' side and the desired gene on the 3' side. During cotransfection, homologous recombination occuring between viral and transfer vector DNA will produce a small percentage of viral genomes in which the polyhedrin gene has been replaced by the desired gene (0.1-5.0%). The wild-type progeny can be differentiated from the recombinant progeny by a conventional viral plaque assay. Recombinants in which the polyhedrin gene has been replaced, can be identified by their occlusion-negative plaque phenotype observed on a background of occlusion-positive wild-type plaques.

Because the polyhedrin gene is a non-essential gene for productive viral infection, another advantage of baculovirus expression vectors is that the recombinants are viable, helper-independent viruses. Also, baculoviruses only infect Lepidopteran insects; thus, they are noninfectious for vertebrates, and are therefore relatively safe genetic manipulation agents.

Thus, baculoviruses have gained popularity as expression vectors because of the advantages presented above. The BEV system is currently being employed in over 700 laboratories for the overexpression and production of many different gene products. To date, more than 50 different genes have now been expressed by employing this system (Luckow, V. A., and M. D. Summers, Bio/Technology 6:47-55 (1988)).

The use of baculovirus vectors relies upon the host cells being derived from Lepidopteran insects. The proteins expressed by the BEVs are, therefore, synthesized, modified and transported in host cells derived from Lepidopteran insects. Most of the genes that have been inserted and produced in the baculovirus expression vector system have been derived from vertebrate species.

NUCLEAR TRANSPORT

Proteins which are produced in the cytoplasm and are destined for the cell nucleus must somehow migrate from the site of their biosynthesis, across the double membrane of the nuclear envelope, into the nucleus. Nuclear proteins of less than 20-40 kilodaltons (kD) in molecular weight will freely diffuse into the nucleus. Recent studies have shown that nuclear proteins larger than 20-40 kD contain specific targeting signals that are required for this nuclear targeting to occur ("nuclear targeting signal sequences": Dingwall, C. and Laskey, R. A., Ann. Rev. Cell Biol. 2:367-390 (1986); Silver, P. and Hall, M., In R. C. Das and P. W. Robbins, (eds.), *Protein transport and orcanelle biosynthesis*, p. 749-769, (1988)).

A number of different viral proteins have been used to elucidate these signals in mammalian cell systems, including SV40 and polyoma virus large T-antigens (Lanford and Butel, Cell 37:801-813 91984); Kalderon et al, Nature 311:33-38 (1984); Richardson et al, Cell 44:77-85 (1986)), SV40 VPI (Wychowski, et al, Gene 37:63-71 (1985)), adenovirus Ela (Lyons, et al, Mol. Cell. Biol. 7:2451-2456 (1987)), and several different influenza virus proteins (Davey, et al, Cell 40:667-675 (1985); Jones, et al, EMBO J. 5:2371-2376 (1986); Greenspan, et al, J. Virol. 62:3020-3026 (1988)). In addition to the above systems, cellular proteins have been used to define nuclear targeting signals in amphibian oocytes (Dingwall, et al, Ann. Rev. Cell Biol. 2:367-390 (1982); Burglin and DeRobertis, EMBO J. 6:2617-2625 (1987)) and in yeast (Hall et al, Cell 36:1057-1965 (1984); Silver, et al, ibid (1984)).

Together, these studies have shown that nuclear targeting signal sequences consist, in general, of short stretches of basic amino acids, often found in alpha helical regions of proteins. Interestingly, nuclear targeting signals in yeast proteins appear to be slightly different from the above cited examples, with two short basic amino acid sequences separated by a short hydrophobic core of basic amino acids. This latter observation suggests that the nuclear targeting signals of higher and lower organisms might be different.

Recently, it was determined that short synthetic peptides can function independently as nuclear targeting localization signals. These signals, when bound to a variety of different non-nuclear proteins, will mediate their nuclear localization (Goldfarb, et al, Nature, 322:641-644 (1986); Lanford, et al, Cell 46:575-582 (1986)). Thus, non-nuclear proteins, can in fact, be targeted into the nucleus by using these signals. Coupled with the development of in vitro assays, this has permitted separation of the nuclear transport mechanism into two distinct steps: a nuclear pore binding step and a translocation step (Newmeyer and Forbes, Cell 52: 641-653 (1988); Richardson, et al, Cell 52:655-664 (1988)). Peptides also have been useful in chemical crosslinking studies, resulting in the identification of cellular proteins that will recognize and bind to them (Adam, et al, Nature 337:276-279 (1989)).

One can envision that a nuclear targeting signal sequence, native to the protein of choice, and not specific for the expression system, might not be efficient in a heterologous host. When using the baculovirus expression vector system, one could predict that a newly synthesized protein would be transported from the cytoplasm to the nucleus more efficiently if a homologous insect baculovirus nuclear targeting signal sequence were employed instead of the signal sequence native to the protein of interest. In fact, nuclear transporting should be enhanced if the nuclear targeting signal sequence is homologous to the host system the protein of choice is being expressed in.

Polyhedrin is a likely candidate for containing a nuclear targeting signal sequence because it has a molecular weight of about 33 kD and it is destined to be transported to the nucleus. If a nuclear targeting signal sequence were found in the polyhedrin protein, then this sequence could be used in the baculovirus expresson vector system to direct the movement of non-nuclear proteins from the cytoplasm to the nucleus.

Data regarding the determination of a putative polyhedrin nuclear targeting signal sequence has recently been generated (Jarvis, et al. In preparation (1989)). The investigator's preliminary data indicated that a minimal nuclear localization signal was located between amino acids 1-30 of the polyhedrin protein. It was also determined that there was a stretch of basic amino acids from amino acid 32 to 36 (Lys-Arg-Lys-Lys-His) which was not an essential part of this signal.

These polyhedrin nuclear targeting signal sequences may be effective in directing the movement of non-nuclear proteins from the cytoplasm to the nucleus when employing the baculovirus expression vector system. An advantage of this technique, is that the isolation and purification of proteins would be simpler if the protein was located in the nucleus as compared to cytoplasmic localization.

Isolation and purification of proteins sequestered into the nucleus by the nuclear targeting signal sequence is easily achieved by employing a standard protocol for isolating nuclei. In simple terms, a significant purification of the recombinantly produced desired protein is achieved by isolating nuclei, thereby leaving behind the unwanted cytoplasmic proteins.

In light of the above mentioned difficulties related to the prior art technology for isolation and purification of proteins, there is a need for a general purification method for proteins which are recombinantly produced in a heterologous expression system. This method should be reproducible, efficient and cost effective, as well as be applicable to a variety of recombinantly produced proteins. The invention disclosed herein presents methods and compositions which allow for the timely, efficient, inexpensive and straightforward purification of a variety of proteins, while perserving funcationality without the worry of degradation.

SUMMARY OF THE INVENTION

In general and overall scope, the present invention provides a method for the isolation and purification of recombinantly produced proteins from a variety of expression systems. This method involves the use of an expression vector which includes a nuclear targeting signal sequence which effectively directs the newly synthesized protein from the cytoplasm to the nucleus. This expression vector also includes cDNA which encodes for the desired protein. More particularly, the present invention describes a method of purifying recombinantly produced proteins which involves the novel use of a cleavage recognition sequence and a viral enzyme which cleaves specifically at a pre-designated cleavage site. The recombinantly synthesized proteins, obtained from this method, are essentially intact and functional. The methods and compositions described herein will be efficient as well as straightforward and will not require extensive equipment or technical experience.

In accordance with the present invention, the recombinant DNA vector which can be used to produce proteins in a variety of host systems includes a DNA region comprising a nuclear targeting signal sequence, a DNA region comprising a cleavage recognition sequence and a DNA region comprising a cDNA sequence coding for a desired protein.

The nuclear targeting signal sequence directs newly translated hybrid or chimera proteins, which possess this targeting sequence, into the nucleus from the cytoplasm. Nuclear targeting signal sequences have been found in a variety of different sources including mammals (Lanford and Butel, Cell 37: 801-813 (1984); Kalderon, et al Nature 311: 33-38 (1984); Richardson, et al Cell 44: 77-85 (1986); Greenspan, et al J. Virol. 62: 3020-3026 (1988), yeast (Hall, et al Cell 36: 1057-1065 (1984); Silver et al PNAS 81: 5951-5955 (1984)), amphibian oocytes (Dingwall et al Cell 30: 449-458 (1982); Burglin and De Robertis EMBO 6: 2617-2625 (1987)), and insects (Jarvias et al In preparation, 1989). The particular targeting signal used for the production of a specific desired protein depends on the expression system as well as the host cells employed. Compatibility among the components described herein optimizes production of the desired protein.

This recombinant DNA vector also includes a DNA region comprising a cleavage recognition sequence. This cleavage recognition sequence may be derived from a viral polyprotein obtained from a potyvirus, a picornavirus, a comovirus or a nepovirus. Specifically, for example, the cleavage recognition sequence derived from a plant potyvirus polyprotein is defined as a conserved heptapeptide amino acid segment or sequence motif. This cleavage amino acid sequence motif is defined as the region of DNA comprised of the amino acids: (Glu)-(Xaa)-(Xaa)-(Tyr)-(Xaa)-(Gln)-(Ser or Gly). 'Xaa' is defined to represent any amino acid at that particular location. The cleavage recognition sequence is recognized and thereby cleaved by a specific viral proteinase. The cleavage site for this viral proteinase is accurately and reproducibly positioned between a (Gln-Ser) or a (Gln-Gly) dipeptide of the conserved heptapeptide amino acid sequence motif.

In addition to the above two components, the recombinant DNA vector includes a DNA region comprising a cDNA sequence coding for a desired protein. Sequences coding for a variety of different genes are known to those skilled in the art and are commercially available from American Type Culture Collection (ATCC, Rockville, Md.). For example, the following is a brief list representing the range of cloned genes or probes available from ATCC: epidermal growth factor receptor, beta-glucuronidase, Y-mos M1 Maloney sacoma virus, tissue-type plasminogen activator, arginosuccinate synthetase, insulin (A and B chain), prolactin, interleukin 1 and 2, colony stimulating factor, tumor necrosis factor, beta-hemoglobulin, interferon, leutinizing hormone, beta-hexosaminidase, coagulation factor VIIIC, transferrin, esterase D, adenosine deaminase, etc. This cDNA sequence is further comprised of nucleotide sequences coding for a desired protein having a deleted 5' untranslated region, and a deleted or mutated translational initiation site. In terms of this invention, amino acid and nucleotide numbers will be used interchangeably with the appropriate conversion factor employed.

For the purpose of this invention, hybrid or chimera proteins are defined as the entire protein translated when using the recombinant DNA vector and its components, which are directionally positioned and in the appropriate reading frame, described herein. The chimera or hybrid protein contains amino acid sequences coding for the nuclear targeting signal sequence, the cleavage recognition sequence and the desired protein, directionally positioned and properly spaced from 5' to 3'.

For enhanced expression and production of the desired protein, this recombinant DNA vector, in addition to the above stated components, includes a DNA region comprising unique signals for the initiation of transcription and translation positioned 5', and in frame, to the DNA region comprising the nuclear targeting signal sequence.

In addition, this recombinant DNA vector includes a DNA region comprising a multiple cloning cassette sequence positioned 3', and in frame, to the DNA region comprising the cleavage recognition sequence and 5' to the DNA region comprising the cDNA sequence coding for the desired protein. Multiple cloning cassette sequence cartridges are commercially available from several different companies (Promega, New England Biolabs, etc). A typical cassette sequence cartridge would include restriction sites for 8-11 different enzymes (i.e. Eco Rl, Sacl, Sma 1, Ava 1, Bam Hl, Xba 1, Hinc II, Acc 1, Sal 1, Pst 1, Hind III, etc.). The availability of these cassette cartridges are known to those skilled in the art.

In addition, this recombinant DNA vector also includes a DNA region comprising a promoter sequence positioned 5' to DNA regions comprising the unique sites for initiation of transcription and translation. The choice of promoters to be included in this recombinant DNA vector would depend on the host system employed. It would therefore be advantageous to employ a compatible promoter with regard to the system in which the desired protein will be produced.

Protein production is enhanced if homologous, therefore compatible targeting signal sequences, as well as promoters, expression systems and host cells are employed. Efficiency of protein production, nuclear targeting and purification is improved by employing homologous and therefore compatible components. For example, production and purification of a specific protein is enhanced if the system employed included a baculovirus expression vector and a baculoviral polyhedrin promoter, along with the cDNA coding for the desired protein, all of which would be transfected or infected into compatible and homologous Lepidopteran insect cells (e.g. Sf9).

Depending on the host system employed, a variety of compatible promoters are available to those skilled in this art. For example, if the investigator was utilizing a baculovirus expression vector and Sf9 Lepidopteran insect host cells, the promoter of choice could be the polyhedrin very late promoter. There are numerous different baculovirus compatible promoters and these are known to those skilled in this art of technology. Choosing one promoter and expression system over another is more done by preference, as there are many different effective combinations of the components involved.

Another example of compatible components is the use of mammalian cell cultures (i.e. chinese hamster, COS and M-6 african green monkey, HeLa cells, etc.) with a compatible yet strong promoter (i.e. thymidine kinase, etc.) used in conjunction with a compatible expression vector system (i.e. p91023-b (Kaufmann vector)).

If the system of choice was yeast, there are numerous yeast expression vectors (i.e. YEp13, pFL1-4, pJDB207, etc) and yeast host strains ( i.e. *Sacchoromycopsis lipolytica. Kluyveromyces lactis,* etc.), as well as a variety of efficient and strong promoters (e.g. the promoters of alcohol dehydrogenase, enolase, glyceraldehyde-3-phosphate dehydrogenase, alkaline phosphatase, etc).

The various techniques which have been successfully applied to the cloning and expression of many heterologous genes in a variety of host systems, employing many different promoters and expression vectors, are known to those skilled in the art of recombinant DNA technology and could be applied to the embodiments described herein. Appropriate positional spacing between the numerous recombinant DNA vector components (directionally positioned 5' to 3') is determined for each specific recombinant DNA vector and this information is included to further optimize the expression and production of the desired protein.

In terms of the nuclear targeting signal sequence, the source can either be derived from a mammalian, amphibian, insect or yeast cell system (see references supra). The choice of the source from which a nuclear targeting signal sequence is derived depends on the selected host system, expression vector and promoter employed. The effectiveness of enhanced foreign protein production depends on the compatibility of the individual components comprising the recombinant DNA vector, as well as, the compatibility of the expression system and host cells employed.

Further in accordance with this invention is a method for producing and isolating a desired protein comprising the steps of: a) infecting or transfecting yeast or eukaryotic cells with a recombinant DNA vector containing an expression system for a specific chimera protein comprising a nuclear targeting signal sequence and a cleavage recognition sequence; b) isolating nuclear components from the infected or transfected yeast or eukaryotic cells; c) extracting total protein from the nuclear components isolated from the infected or transfected yeast or eukaryotic cells; d) attaching the chimera protein to an affinity matrix embedded with antibodies directed against the nuclear targeting signal sequence portion of the chimera protein; e) releasing the desired protein from the chimera protein attached to the affinity matrix with an enzyme that specifically cleaves at the cleavage recognition sequence; and f) collecting the released 3' positioned desired protein from the chimera protein.

In terms of infecting or transfecting yeast or eukaryotic cells with a recombinant DNA vector, these techniques are standard and known to those skilled in the art of recombinant DNA technology. In terms of transfecting cells with the recombinant DNA vector described above, this invention could also be applied for the production of stable cell lines which are, by definition, continuously producing the specific chimera protein. The production of cell lines with stably integrated recombinant DNA vectors has been described extensively in the literature, practiced for years, and is therefore known to those skilled in the art.

In terms of isolating nuclei from the infected or transfected yeast or eukaryotic cells, these techniques are standard and available to those skilled in the art of nuclear protein purification. Extraction of total nuclear proteins, isolated from the infected or transfected cells, involve techniques which are standard, routinely employed and known to those skilled in the art.

In terms of attaching the newly translated chimera protein to an affinity matrix, this matrix can be comprised of any type suitable for allowing a specific interaction between an antibody and an antigen. There are many choices of different affinity matrixes available to those skilled in the art, including, for example, a chromatographic column or protein A-Sepharose beads.

The affinity matrix component is embedded with antibodies directed against the specific nuclear targeting signal sequence for the purpose of interacting with chimera proteins containing that specific nuclear targeting signal sequence. The antibodies generated against the nuclear targeting signal sequence may either be polyclonal or monoclonal in nature. The generation of such antibodies employs standard techniques known to those skilled in the art of antibody production.

In terms of the above description, either Sepharose beads or a chromatographic column, both of which are embedded with antibodies directed against the nuclear targeting signal sequence, can be employed for the isolation of the newly translated protein. The chimera proteins can be separated from other extracted total nuclear proteins through the formation of an antibody-antigen complex between an antigenic portion of the chimera protein and antibodies specifically generated against the nuclear targeting signal sequence. This interaction only binds the desired chimera proteins containing a nuclear targeting signal sequence thereby allowing the unwanted nuclear proteins to be washed away.

A viral proteinase is added to the affinity matrix composition once the chimera proteins have specifically interacted with the antibodies embedded in the matrix. The viral proteinase cleaves at a specific predetermined cleavage recognition sequence. This cleavage recognition sequence may be derived from a viral polyprotein obtained from a potyvirus, a picornavirus, a comovirus or a nepovirus. For example, if the cleavage recognition sequence is derived from a Tobacco etch virus polyprotein potyvirus then this sequence comprises a conserved heptapeptide amino acid sequence motif of (Glu)-(Xaa)-(Xaa)-(Tyr)-(Xaa)-(Gln)-(Ser or Gly). This viral proteinase specifically cleaves between the dipeptide (Gln-Ser) or (Gln-Gly). This dipeptide is located within the conserved heptapeptide amino acid segment which comprises the cleavage recognition sequence. Once the proteinase cleaves between the specific dipeptide of the cleavage recognition sequence, the 3' portion of the cleavage site is released from the matrix. The released portion of the chimera protein is the desired protein.

Further in accordance with the method for producing and isolating a desired protein involves removing the cleavage enzyme from the admixture containing the released 3' positioned desired protein. The removal of the cleavage enzyme is achieved by several methods known to those skilled in the art. One method for removing the cleavage enzyme involves employing a second immunoaffinity adsorption column containing anti-cleavage enzyme antibodies. The product (desired protein) can be harvested from the flow-through solution. Another method for removal of the cleavage enzyme employs sedimentation if the enzyme is the Tobacco etch virus 49 kD proteinase which is isolated from infected plants in the form of insoluble inclusion bodies. Either one of these methods are effective for removing the cleavage enzyme from the admixture.

Thus, employing this method allows for the production and isolation of most desired proteins without undue experimentation and manipulation.

A: Construction of Polyhedrin-Beta-Galactosidase Fusion Genes Employing Deletional Mutagenesis The plasmid pAcP(E5-S) contains an intact polyhedrin gene, including the promoter, coding sequences and 3' noncoding sequences. This parent plasmid will be used to produce truncated plasmids that encode 11, 22, 28, 30, 57 or 110 amino acids of polyhedrin. The truncated portions of the polyhedrin gene will then be ligated to the coding region for the cytoplasmic protein, B-galactosidase (B-gal). Each of the truncated polyhedrin-B-gal fusion plasmids will be sequenced in order to determine the reading frame.

B: Hypothetical Depiction of the AcNPV Polyhedrin Nuclear Targeting Signal Sequence Depicted herein is a hypothetical prediction for the location of the polyhedrin nuclear targeting signal sequence.

FIG. 2A

Step 1: Outline of the Construction of a Model Expression Vector Used for Recombinant Protein Production The construction of a model expression vector which would be employed for recombinant protein production is outlined. '[5']' is defined as the region located upstream or to the left of the compared component; 'ATG' is defined as a genetically positioned site that signals the initiation of translation (ATG codes for methionine); 'NTSS' (nuclear targeting signal sequence) is defined as a genetically positioned region which signals the re-localization of newly synthesized cytoplasmic proteins from the cytoplasm to the nucleus; 'CRS' (cleavage recognition sequence) is defined as a genetically positioned region which contains the sequence that is specifically recognized by the viral cleavage enzyme; 'MCCS' is defined as a genetically positioned region which contains a multiple cloning cassette sequence; 'cDNA' is defined as the DNA sequences which specifically encodes for the desired protein that is to be produced and purified; '[3']' is defined as the region located downstream or to the right of the compared component.

FIG. 2B

Figure 2A:
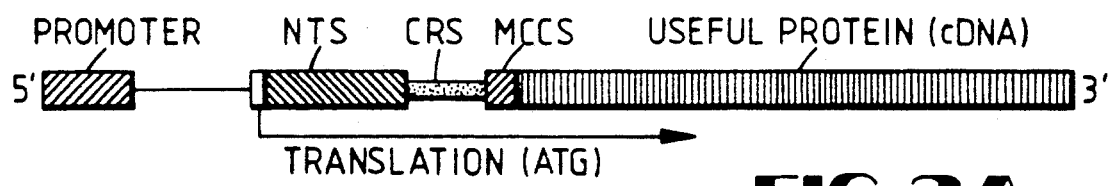
Figure 2B:
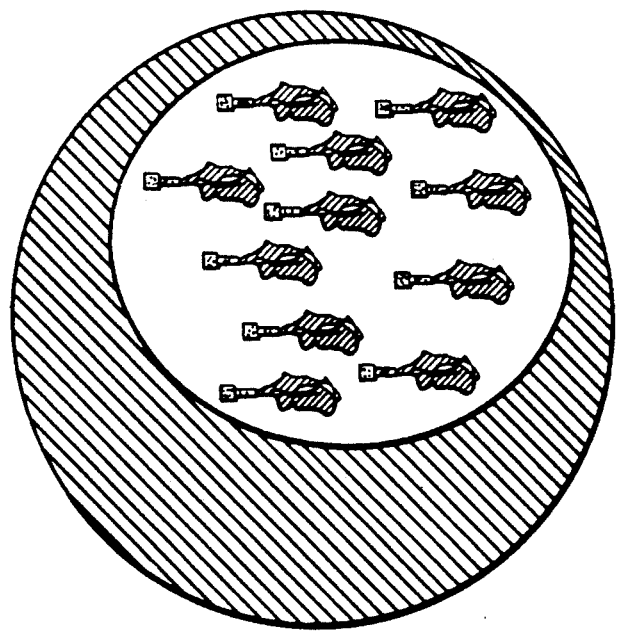
Figure 2C:
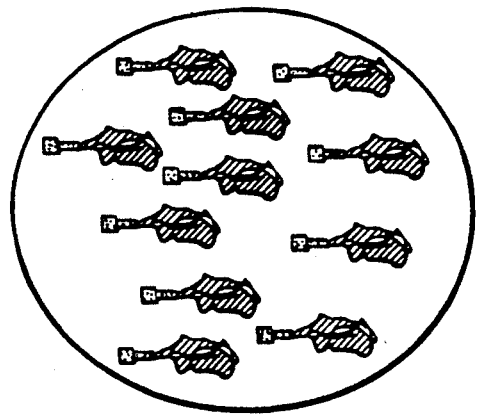
Figure 2C:
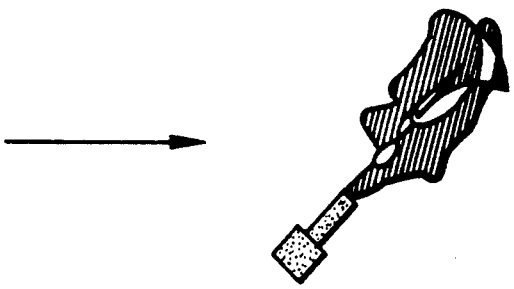
Figure 2D:
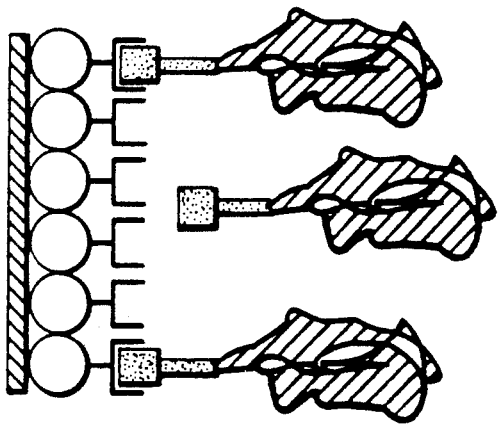
Figure 2E:
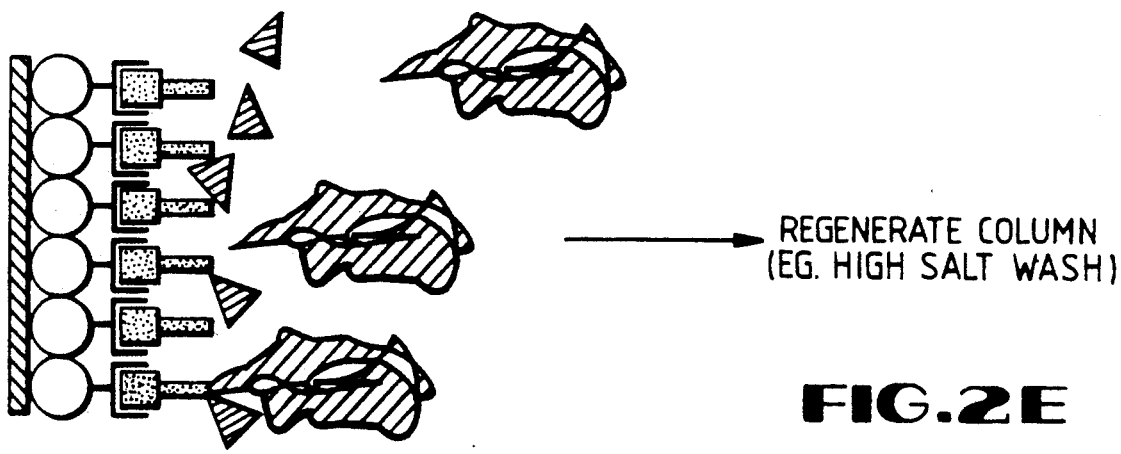
Figure 2F:
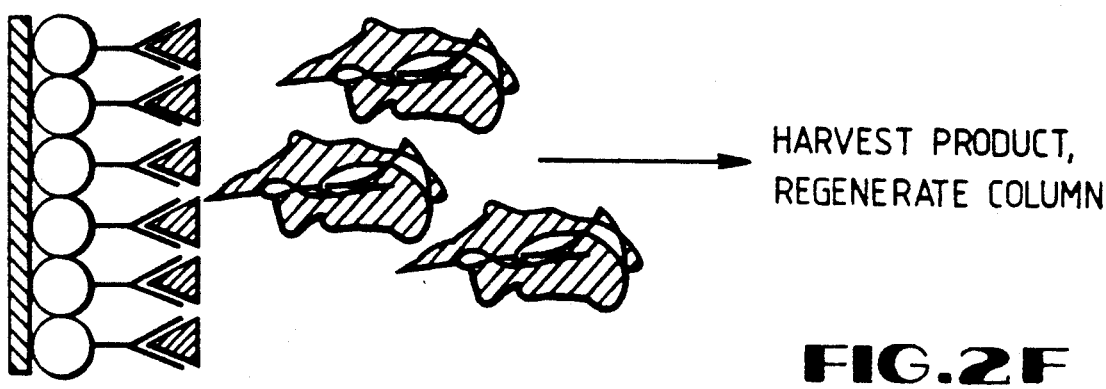

Steps 2-6: Schematic Generic Purification of Recombinantly Produced Model Proteins The recombinantly produced model protein, including all of the salient features described above, are presented in this drawing. The definitions of 5', ATG, NTSS, CRS, MCCS, cDNA and 3' are described above. Briefly, once the model protein is synthesized, the model protein is directed out of the cytoplasm and targeted to the nucleus by the NTSS (Step 2; FIG. 2B). The nuclei are isolated from the cellular source and total nuclear proteins are extracted from the nuclei (Step 3; FIG. 2C). The total nuclear proteins are further separated by interaction with a solid matrix embedded with antibodies directed against the NTSS (Step 4; FIG. 2D). The proteins containing the NTSS will bind to the solid matrix through an antibody-antigen complex. The CRS-specific-enzyme is then added and cleavage occurs at the predetermined site (Step 5; FIG. 2E). This cleavage action releases the composition 3' to the cleavage site, thereby allowing the recovery of the recombinantly produced model protein after removal of the CRS-specific-enzyme (Step 6; FIG. 2F).

DETAILED DESCRIPTION OF THE PREFERRED EMBODIMENTS

General Approach for Determining the Location of the Nuclear Targeting Signal Sequences in the Polyhedrin Protein Defined fragments of the polyhedrin protein were tested for nuclear targeting signals by constructing hybrid genes in which various lengths of the polyhedrin coding sequence are fused to the sequence encoding B-galactosidase (B-gal) of *E. coli*. The hybrid genes were used to construct BEVs to express the recombinant products in insect cells. The intracellular distributions of the recombinant products were determined by immunofluorescence and radioimmuno-precipitation, using anti-B-gal as a probe. Wild type B-gal is a cytoplasmic protein, thus, any protein localized within the nucleus contains a fragment of the polyhedrin protein that has a nuclear targeting signal. The precise location of the nuclear targeting signal was defined and characterized in further detail by site-directed mutagenesis (Zoller and Smith, Methods Enzymol. 100:468–500 (1983)).

Construction of Polyhedrin-B-Galactosidase Fusion Genes

Figures 1A, 1B:
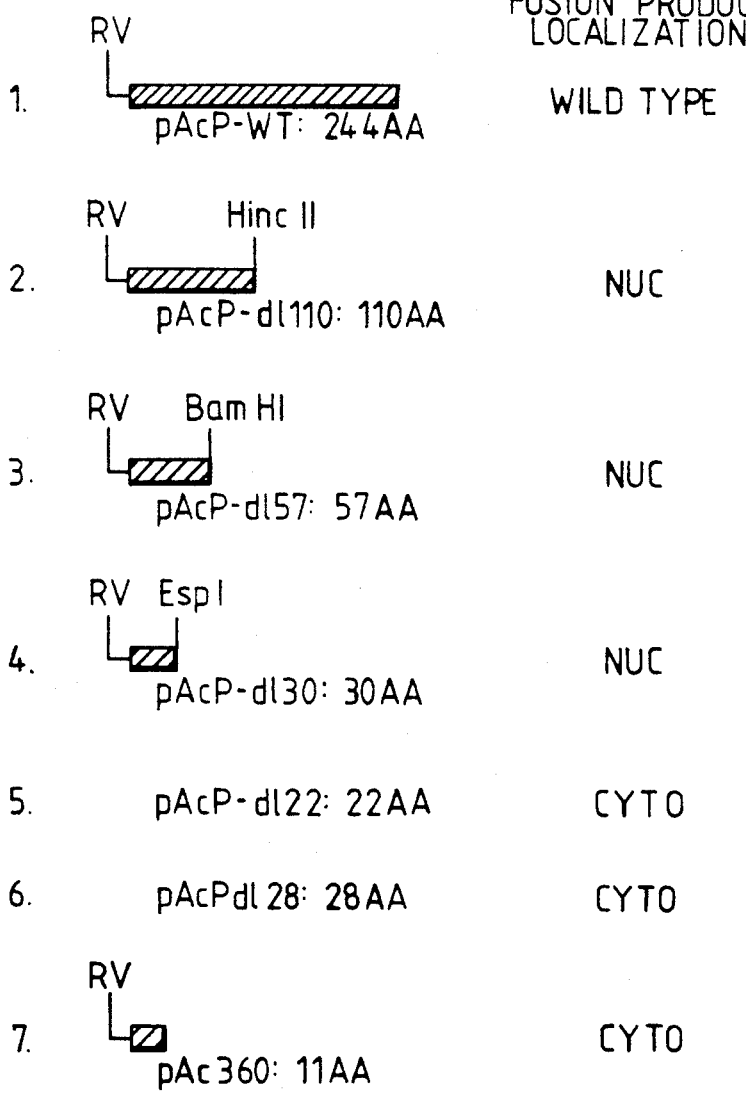
FIG. 1 (Parts A and B).

A series of truncated polyhedrin containing plasmids were generated in order to localize the polyhedrin nuclear targeting signal sequence. This was performed as described below. The plasmid pAcP(E5-S) contained an intact polyhedrin gene, as well as the promoter, coding sequences and 3' noncoding sequences. This plasmid was used to produce a series of truncated plasmids which encode for 19, 30, 57, 110 or 212 amino acids of polyhedrin (FIG. 1A). To generate these truncated plasmids, pAcP(E5-S) was digested with Sca 1, Esp 1, Bam Hl, Hinc II or Kpn 1, treated with alkaline phosphatase and appropriate phosphorylated Sma 1 linkers were inserted by blunt-end ligation. The vector was blunt-ended either by using DNA polymerase to fill in 5' overhangs or by using mung bean nuclease to remove 3' overhangs. One of the three types of commercially available Sma 1 linkers (New England Biolabs) were chosen to maintain the open reading frame between the polyhedrin sequence and a B-gal sequence which was then inserted at the newly generated Sma 1 site. After ligation, the constructs were digested with Sma 1, phenol-extracted, ethanol precipitated and re-ligated. This step was included to eliminate multiple copies of Sma 1 linkers. Bacterial transformation, screening by restriction mapping, extraction and purification of plasmid DNA were accomplished by standard recombinant DNA techniques (Maniatis, et al, *Molecular cloning: A laboratory manual*, Cold Spring Harbor Press, Cold Spring Harbor, N.Y. (1982)).

Each of the plasmids resulting from the manipulations described above contained a truncated portion of the polyhedrin gene. These truncated portions of the polyhedrin gene began at an Eco RV site which was located at the beginning of the promoter and they end with a Sma 1 site which was positioned after 19, 30, 57, 110 and 212 amino acids. These truncated genes were removed by digestion with Eco RV and Sma 1, gel purified and subcloned into a baculovirus transfer vector, pAc610 (Luckow and Summers, Bio-technology 6:47–55 (1988a)). This baculovirus transfer vector contained the viral flanking sequences which were necessary for the production of viral recombinants through homologous recombination. Once the desired subclones were produced, a Sma 1 - Pst 1 fragment from pMC1871 (Shapira, et al, Gene 25:71-82 (1983)) was inserted. This pMC1871 Sma 1 -Pst 1 fragment contained the sequences encoding for B-galactosidase, (started at amino acid 9 and proceeded through its natural termination site). In each of the final constructs, the truncated polyhedrin sequence was fused to B-gal through a bridge consisting of the sequence [Ser-Pro-Gly-Asp-Pro], due to the presence of the Sma 1 linker. After subcloning the appropriate fragments into M13 vectors, the nucleotide sequences of these junctions were confirmed by dideoxynucleotide sequencing. The verified constructs were used to produce recombinant baculoviruses which were further used in studies to pinpoint the nuclear targeting signal sequence.

The Sf9 clone of the IPLB-Sf21 AE cell line, derived from Spodoptera frugiperda (Vaugn, et al In Vitro 13:213-217 (1977)), was used in these localization experiments because it was most often employed for foreign gene expression by BEVs. Individual Sf9 cell cultures were cotransfected with wild type baculovirus DNA plus each of the individual polyhedrin-B-gal fusion plasmids. At about 5 days post-transfection, the growth medium was harvested, clarified and used for plaque assays on fresh Sf9 cell monolayers. Assuming that the added polyhedrin sequence did not inactivate B-gal activity, the B-gal portion of the hybrid proteins should therefore remain enzymatically active. The chromogenic substrate 'x-gal' (Promega-Biotech), which turns blue when it reacted with B-gal, was added to the agarose overlay in these plaque assays. Recombinant viral plaques were identified on the basis of their blue color. These B-gal containing plasmids were isolated and subjected to two additional rounds of plaque purification. If B-gal activity was inactivated in one or more of the constructs, recombinants were identified on the basis of their occlusion-negative plaque phenotype. Once plaque purified, the working virus stocks were prepared in Sf9 cells and stored using standard methods (Summers and Smith, TAES Bull. 1555 (1987)).

Subcellular Distribution of Fusion Products Indirect immunofluorescence of polyhedrin-B-gal fusion proteins The subcellular, nuclear versus cytoplasmic distribution of the fusion products encoded by each of the recombinant polyhedrin-B-gal plasmids were determined by indirect immunofluorescence. If the polyhedrin portion of the fusion plasmid contained a sequence which could direct the localization of a protein from the cytoplasm to the nucleus, then nuclear immunofluorescence was detected. This type of indirect assay was used to initially screen the various truncated polyhedrin-B-gal plasmids.

Indirect immunofluorescence involved infecting Sf9 cells with virus negative medium, wild type baculovirus or a recombinant baculovirus. The cells were then incubated for 24 hours post infection, washed with PHEM buffer (60 mM PIPES, 25 mM HEPES, 10 mM EGTA, 2 mM MgC12, pH 6.9) and fixed in fresh formaldehyde. The fixed cells were further washed with PHEM, permeabilized with Triton-X-100 and rewashed with Dulbecco's phosphate buffered saline (DPBS). The cells were treated either with mouse anti-B-galactosidase (primary antibody:B-gal; Promega-Biotech) or with a polyclonal control antiserum, PAb 419 (directed against the SV40 large T-antigen) which was diluted into DPBS containing 2% normal goat serum. Excess antibody was washed away, and fluorescein-isothiocyanate (FITC)-conjugated goat-anti-mouse-IgG (Organon Teknika) was used as a secondary antibody. The cells were washed, stained with a DNA specific stain (DAPI), rewashed and mounted for analysis and photography under fluorescent microscopy. It was possible to identify individual nuclei because an interaction between DNA and the DNA specific stain (DAPI) was indicated by the color blue.

By employing different excitation/emission filters in the microscope, the regions of the cell which contained the fusion protein were stained green. Thus, by employing the stain DAPI, the FITC-conjugated second antibody, and two different filters, the investigator differentiated the nucleus from the cytoplasm and then looked for immunofluorescence in one of these two regions. Initial experiments have shown that neither mock nor wild type baculovirus infected Sf9 cells stained with anti-B-gal plus secondary antibody. Thus, the levels of endogenous or induced B-gal will not interfere with this type of analysis.

Quantitative analysis of the intracellular distribution of the polyhedrin-B-gal fusion proteins Quantitative analysis of the intracellular distribution of the polyhedrin-B-gal fusion proteins was achieved by using a different method. This method involved radioimmunoprecipitation of proteins isolated from nuclear or cytoplasmic fractions of infected cells. Exponentially growing Sf9 cells were infected with the individual recombinant viruses and further incubated 20 to 44 hours post infection. The cells were labelled with 100 uCi of 35-S-methionine per ml of methionine free medium either 20-24 or 44-48 hours post infection. Once the labelling period was completed, the medium was removed and the cells were treated with Tris-buffered NP40 (0.5-1.0%, pH 6.0-6.5, 10 minutes, 4° C.). The supernatant was harvested and clarified; and was defined as the 'cytoplasmic' fraction while the pellet comprised the 'nuclear' fraction. The nuclei were suspended in detergent containing buffer whereupon the fractions were sonicated, clarified and immunoprecipitated. Each sample was split in half, and one half of the sample was immunoprecipitated with PAb 419 (control antiserum) while the other half was immnuo-precipitated with anti-B-gal. The immunoprecipitates were absorbed onto fixed S. aureus cells, washed, denatured and resolved by gel electrophoresis.

Specific B-gal reactive bands were detected by Coomassie blue staining. The bands of interest were excised from the gel, solubilized and the amount of radioactivity was determined by liquid scintillation spectroscopy. The specificity of the immunoprecipitates were verified by control antisera PAb 419 and mock infected Sf9 cells. Wild type baculovirus and VL720-B-gal infected cells served as positive controls for nuclear (polyhedrin) and cytoplasmic (B-gal) proteins, respectively. The data were quantified and expressed as the percentage of protein found in the nuclear fractions versus the amount found in the cytoplasmic fractions.

Defining the location of the putative nuclear targeting signal once the general domain is determined Once a polyhedrin nuclear targeting signal sequence is found in one of the truncated fusion plasmids, then the minimum number of amino acids capable of nuclear transport will be defined. This can be accomplished by a variety of techniques known to those skilled in the art. For example, if the signal falls within a large domain (i.e. such as the one between amino acids 110 and 212), the exonuclease Bal 31 can be used to generate a series of deletions which can then be used to map the signal to a smaller subregion within that domain. This would require the isolation of several deletions of varying sizes and a number of individual plasmids in each of the above described size classes. Each of these deletion mutants must be screened for B-gal activity to identify in-frame deletions.

Another approach which can be employed if the signal falls within a shorter domain, would be to use oligonucleotide directed mutagenesis (Zoller and Smith, ibid (1983)) to alter specific amino acid residues in the putative nuclear targeting signal. However, this cannot be accomplished until the putative nuclear targeting signal has been determined to fall within a relatively short sequence.

A complementary approach which could be used to show the autonomous nature of a putative signal, would be to synthesize peptides corresponding to the signal, cross link them to various non-nuclear proteins and demonstrate that they are capable of mediating nuclear targeting/localization of those non-nuclear proteins.

Description of a viral cleavage recognition cassette sequence and specific proteinase A number of plant and animal viruses code for at least one proteinase which processes a primary translation product to a mature product (Krausslich and Wimmer, Ann. Rev. of Biochem., 57: 701-754 (1988)). Viruses possessing a single-stranded RNA genome such as the potyviridae, comoviridae and picornaviridae, code for a proteinase which catalyzes most of the specific cleavages of the genome derived polyprotein to functional gene products (Carrington and Dougherty, Virology, 160:355-362 (1987)).

Tobacco etch virus (TEV), a member of the potato virus Y group is a rod-shaped virus which infects a number of hosts. The genome is organized as a single translational unit capable of being expressed as a 346 kD polyprotein. Among the genomic organization for the TEV are sequences coding for a 49 kD proteinase. All potyvirus genomes that have been sequenced encode an analogue to the TEV 49 Kd proteinase. The TEV 49 kD active protein can be purified from infected plants in the insoluble form (Carrington and Dougherty, J. of Virol. 61: 2540-2548 (1987)).

During the TEV genome expression, the 49 kD proteinase autocatalytically releases from the polyprotein and cleaves in trans at three other sites to yield five virus gene products. In the polyprotein, these gene product boundaries are delineated by the sequence . . . (Glu)-(Xaa)-(Xaa)-(Tyr)-(Xaa)-(Gln-Ser) or (Gln-Gly). Cleavage occurs between the (Gln-Ser) or (Gln-Gly) dipeptides (Carrington and Dougherty, ibid (1987)). Insertion of an oligonucleotide which encodes the heptapeptide amino acid segment at the 54 kD/ 30kD protein boundary ( . . . Glu-Asn-Leu-Tyr-Phe-Gln-Ser . . . ) generates a functional cleavage site (Carrington and Dougherty, PNAS, 85: 3391-3395 (1988)).

Carrington et al (J of Virology, 62(7): 2313-2320, (1988)) altered the amino acid residue Gln which was the predicted cleavage site. The altered Gln sites were not cleaved by the 49 kD proteinase. A series of synthetic polyproteins that contained the 49 kD proteinase linked to adjoining proteins via defective cleavage sites were expressed, and their proteolytic activities were analyzed. The results have shown that all five sites in the polyprotein which conform to the conserved sequence motif are functional as proteolytic substrate sites. The investigators found that the TEV 49 kD proteinase was catalytically active within a polyprotein and that cleavage in cis at the 49 kD proteinase amino and carboxyl terminal borders appeared not to require a specific sequential order in vitro. Therefore, as part of a polyprotein, the proteinase was found to exhibit cis (intramolecular) and trans (intermolecular) activity.

To identify sequences in the TEV polyprotein sufficient to confer 49 kD proteinase mediated substrate activity, amino acid sequences bordering two TEV cleavage sites were introduced into proteins at sites not normally processed by the proteinase. The results demonstrated that TEV cleavage sites were transferable from one protein to another and that as few as 7 amino acid residues surrounding an authentic polyprotein junction can define a functional cleavage site (Carrington and Dougherty, PNAS, 85:3391-3395, (1988)).

The examples which follow are illustrative of laboratory techniques found by the present inventor to constitute preferred modes for practicing various aspects of the invention. However, those of skill in the art, in light of the present disclosure, will appreciate that various modifications and alterations can be made in the structuring and carrying out of the invention, and still remain within the spirit and scope of the invention.

EXAMPLE 1

Elucidation of nuclear targeting signal in baculovirus protein polyhedrin

Polyhedrin accumulates in large amounts within the nuclei of insect cells infected with *Autographa californica* nuclear polyhedrosis virus (AcNPV). Increasing lengths of the polyhedrin coding sequence were fused in frame to the sequence encoding the cytoplasmic protein, B-galactosidase (B-gal). Each hybrid gene was engineered into a recombinant baculovirus for expression in insect cells. The subcellular distribution of the fusion products was determined by indirect immunofluorescence using anti-B-gal antibody as the probe. The results demonstrated that fusion proteins containing polyhedrin amino acids 1 to 11, 22, or 28 were cytoplasmic, while those fusion proteins containing amino acids 1 to 30, 57 or 110 were nuclear (FIG. 1, A; Table 1). The conclusions from this study were: 1). AcNPV polyhedrin contains a nuclear targeting signal sequence; 2). This signal is found between amino acids 11-30 of polyhedrin; 3). Amino acids 32-36 most closely resemble a known nuclear targeting signal sequence, but are not a requirement for nuclear localization in Sf9 cells. FIG. 1, B presents a hypothetical depiction of the AcNPV polyhedrin nuclear targeting signal sequence. Of interest, Table 1 presents evidence that insect nuclear targeting signals are more efficient in insect cells than mammalian nuclear targeting signals (Table 1, WT(E2)* and 941-SVT*).

TABLE 1

| VIRUS | 24 HOUR PI | | 48 HOUR PI | |
|---|---|---|---|---|
| | CYTO (%) | NUC (%) | CYTP (%) | NUC (%) |
| Ac-B-gal | 22,709 (95) | 1,1026 (5) | 103,580 (96) | 4,256 (4) |
| AcP-11 | 83,293 (99) | 1,023 (1) | 404,540 (97) | 11,767 (3) |
| AcP-22 | 200,140 (99) | 1,327 (1) | 104,310 (98) | 2,701 (2) |
| AcP-28 | 149,340 (99) | 1,191 (1) | 308,615 (98) | 6,994 (2) |

TABLE 1-continued

| VIRUS | 24 HOUR PI | | 48 HOUR PI | |
|---|---|---|---|---|
| | CYTO (%) | NUC (%) | CYTP (%) | NUC (%) |
| AcP-30 | 10,728 (36) | 19,417 (64) | 4,024 (14) | 25,794 (86) |
| AcP-57 | 29,696 (32) | 64,184 (68) | 4,203 (4) | 96,213 (96) |
| AcP-110 | 13,217 (18) | 58,858 (82) | 4,285 (3) | 135,778 (97) |
| WT(EZ)* | 24,052 (32) | 51,670 (68)* | 26,674 (8) | 323,940 (92)* |
| 941-SVT* | 28,384 (84) | 5,466 (16)* | 44,757 (42) | 61,216 (58)* |

EXAMPLE 2

Putative Polyhedrin Nuclear Targeting Signal Sequence

Nuclear targeting signal sequences have been defined in a variety of different sources ranging from SV40, polyoma virus large T-antigens, SV40 VP1, adenovirus E1a and several different influenza virus proteins. Cellular proteins have been used to define nuclear targeting signal sequences in amphibian oocytes and in yeast. Together, these studies have shown that nuclear targeting signal sequences consist, in general of short stretches of basic amino acids, often found in alpha helical regions of the proteins (Table 2). Interestingly, nuclear targeting signal sequences in yeast proteins appear to be slightly different, with two short basic amino acid sequences separated by a short hydrophobic core of basic amino acids. This latter observation suggests that the nuclear targeting signal sequences of higher and lower organisms might be different.

Analysis of the polyhedrin coding region for 'conserved' putative nuclear targeting signal sequences demonstrated the existence of a putative polyhedrin signal located within the first 40 amino acids of polyhedrin from 6 different baculovirus (Table 2). Jarvis, et al. (In preparation, (1989)) have demonstrated that, although this signal displays known nuclear targeting characteristics (i.e. 32 . . . lys-arg-lys-lys-his . . . 39), none of amino acids 32-36 are required for nuclear localization in Sf9 cells (Table 2).

TABLE 2

| Putative Polyhedrin Nuclear Transport Signal | | | |
|---|---|---|---|
| Reported Signals | | | |
| SV40 nT | 126-pro— | lys—lys—lys—arg—lys— | val-132 |
| SV40 cT | 126-pro | lys—asn—lys—arg—lys— | val-132 |
| SV40 VP1 | 1-ala— | pro—thr—lys—arg—lys— | gly-7 |
| Py nT | 280-pro— | lys—lys—ala—arg—glu— | asp-286 |
| | 190-ser— | arg—lys—arg—pro—arg— | pro-196 |
| Ad E1a | 282- | lys—arg—pro—arg—pro— | -286 |
| Nplasmin | 162-ala | lys—lys—lys—lys—leu | asp—lys-169 |
| MAT-å-2 | 2-asn— | lys—ile—pro—ile—lys— | asp-8 |
| Flu NP | 341-leu— | arg—val—leu—phe—ser—ile—arg—gly-349? | |
| Putative polyhedrin signals: | | | |
| AcMNPV | 30-asn—ala— | lys—arg—lys—lys—his— | phe—ala—glu-39? |
| GmMNPV | 30-asn—ala— | lys—arg—lys—lys—his— | leu—glx—glx-39? |
| OpMNPV | 30-asn—ala— | lys—arg—lys—lys—his— | leu—leu—glu-39? |
| LdMNPV | 30-gln—ala— | lys—arg—gln—lys—his— | leu—gln—glu-39? |
| BmSNPV | 30-asn—ala— | lys—arg—lys—lys—his— | leu—ile—glu-39? |
| OpSNPV | 31-asn—ala— | lys—arg—lys—lys—his— | gln—ile—glu-40? |

EXAMPLE 3

Schematic purification of recombinantly produced foreign proteins

The recombinant DNA vector depicted in FIG. 2, (Step 1; FIG. 2A) which will be employed in a variety of different host cells is comprised of the following components positioned directionally from 5' to 3', spaced appropriately and in the proper reading frame: a promoter which is efficient and compatible with the expression system and host cells; a unique signal for initiation of translation; a nuclear targeting signal sequence compatible with the host and expression system; a cleavage recognition sequence; a multiple cloning cassette sequence; and, a cDNA sequence coding for a desired protein with the 5' untranslated region and the endogenous methionine being either deleted or mutated.

As depicted in FIG. 2 (Steps 2-6; FIGS. 2B-2F), the recombinant DNA vector is then infected or transfected into the compatible host cells. Newly synthesized cytoplasmic proteins are transcribed and the chimera proteins which contain the nuclear targeting signal sequence are directed to the nucleus (Step 2; FIG. 2B). Nuclei are then isolated from the infected or transfected cells and total nuclear protein is extracted (Step 3; FIG. 2C). The total nuclear protein composition is then allowed to interact with an affinity matrix (either Sepharose beads or a chromatographic column) which is embedded with antibodies (monoclonal or polyclonal) directed against the nuclear targeting signal sequence (Step 4; FIG. 2D). The antigen-antibody interaction selectively attaches the chimera proteins to the affinity matrix and allows non-desired proteins to be separated away. Once the chimera protein is bound to the affinity matrix, a viral proteinase is added (Step 5; FIG. 2E) This viral proteinase is highly specific for a dipeptide sequence found in the cleavage recognition sequence thereby cleaving and releasing the desired protein from the chimera protein composition. The viral proteinase is separated from the admixture (Step 6; FIG. 2F). This method of producing and isolating desired proteins in a compatible system requires few, if any, modifications or variations from one protein to the next.

While the compositions and methods of this invention have been described in terms of preferred embodiments, it will be apparent to those of skill in the art that variations and modifications may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for producing and isolating a desired protein comprising the steps of:
   infecting or transfecting Lepidopteran cells with a recombinant DNA expression vector for a chimera protein which comprises the following components directionally positioned 5' to 3', and operatively linked to a unique signal for initiation of translation; a DNA sequence consisting essentially of baculovirus polyhedrin nucleotides 1-330, and DNA encoding a viral protease cleavage recognition sequence consisting essentially of heptapeptide amino acid sequence (Glu)-(Xaa)-(Xaa)-Tyr)-(Xaa)-(Gln)-Ser or Gly), both of which are located immediately 5', and operatively linked, to a DNA sequence which codes for a desired protein;
   isolating nuclei from the infected or transfected Lepidopteran cells;
   (c) extracting total protein from the nuclei;
   d) attaching the chimera protein to an affinity matrix embedded with antibodies directed against baculovirus polyhedrin portion of the chimera protein;
   e) releasing the desired protein from the chimera protein attached to the affinity matrix with a 49 kD proteinase from Tobacco etch virus that specifically cleaves at the viral protease cleavage recognition sequence; and
   f) collecting the released desired protein.

2. The method for producing and isolating the desired protein in claim 1 wherein the antibodies, directed against the nuclear targeting signal sequence, are polyclonal or monoclonal.

3. The method for producing and isolating the desired protein in claim 1 wherein the affinity matrix comprises Sepharose beads or a chromatographic column.

4. The method for producing and isolating the desired protein of claim 3 wherein the affinity matrix comprises protein A-Sepharose beads.

5. The method for producing and isolating the desired protein of claim 1 wherein the enzyme is removed from the admixture containing the released desired protein.

6. A DNA vector comprising the following components directionally positioned, while maintaining the appropriate reading frame, from 5' to 3':
   a) a DNA region consisting essentially of baculovirus polyhedrin nucleotides 1-330;
   b) a DNA region encoding a viral protease cleavage recognition sequence consisting essentially of heptapeptide amino acid sequence (Glu)-(Xaa)-(Xaa)-(Tyr)-(Xaa)-(Gln)-(Ser or Gly); and
   c) a DNA region encoding a cloning restriction site available for insertion of a DNA sequence coding for a desired protein.

7. The DNA vector of claim 6 further comprising a promoter positioned 5' and operatively linked to the DNA region encoding the unique site for initiation of translation.

8. The DNA vector of claim 6 wherein the cloning restriction site comprises a multiple cloning cassette sequence positioned 3' and operatively linked to the DNA region encoding the viral protease cleavage recognition sequence.

9. The DNA vector of claim 6 wherein the cloning restriction site is selected from the group consisting of Eco R1, Sac1, Sma 1, Ava 1, Bam H1, Xba 1, Hinc II, Acc 1, Sal 1, Pst 1, and Hind III.

10. The DNA vector of claim 6 which further includes a DNA region encoding a desired protein and inserted at the cloning restriction site.

11. A Lepidopteran insect cell produced by transfecting or infecting Lepidopteran insect cells with a recombinant baculovirus vector which comprises the following components directionally positioned 5' to 3', and operatively linked, to a unique signal for initiation of translation:
   a) a DNA region consisting essentially of baculovirus polyhedrin nucleotides 1-330;
   b) a DNA region encoding a viral protease cleavage recognition sequence consisting essentially of heptapeptide amino acid sequence (Glu)-(Xaa)-(Xaa)-(Tyr)-(Xaa)-(Gln)-(Ser or Gly); and
   c) a DNA region encoding a desired protein.

* * * * *

UNITED STATES PATENT AND TRADEMARK OFFICE
CERTIFICATE OF CORRECTION

PATENT NO. : 5,179,007
DATED : January 12, 1993
INVENTOR(S) : Donald L. Jarvis, et al.

It is certified that error appears in the above-indentified patent and that said Letters Patent is hereby corrected as shown below:

Column 9, Line 45, change "FIG. 2B" to -- FIGS. 2B-2F --.

Column 17:

Claim 1, Line 4, insert -- a) -- before "infecting".

Claim 1, Line 9, change ";" to -- : --.

Claim 1, Line 13, insert -- ( -- before "Tyr)-".

Claim 1, Line 14, insert -- ( -- before "Ser".

Claim 1, Line 17, insert -- b) -- before "isolating".

Claim 1, Line 19, delete "(" before "c)".

Signed and Sealed this

First Day of February, 1994

Attest:

BRUCE LEHMAN

Attesting Officer

Commissioner of Patents and Trademarks